United States Patent
Patel

(10) Patent No.: US 9,480,770 B2
(45) Date of Patent: *Nov. 1, 2016

(54) METHODS FOR PREPARATION OF MEDICAL DRESSING CONTAINING ANTIMICROBIAL AGENT

(71) Applicant: Covidien LP, Mansfield, MA (US)

(72) Inventor: Harish A. Patel, Norfolk, MA (US)

(73) Assignee: Covidien LP, Mansfield, MA (US)

(*) Notice: Subject to any disclaimer, the term of this patent is extended or adjusted under 35 U.S.C. 154(b) by 222 days.

This patent is subject to a terminal disclaimer.

(21) Appl. No.: 14/192,937

(22) Filed: Feb. 28, 2014

(65) Prior Publication Data

US 2014/0178564 A1    Jun. 26, 2014

Related U.S. Application Data

(63) Continuation of application No. 13/330,092, filed on Dec. 19, 2011, now Pat. No. 8,672,906, which is a continuation of application No. 10/278,072, filed on Oct. 23, 2002, now Pat. No. 8,100,872.

(51) Int. Cl.
*A61F 13/00* (2006.01)
*A61L 15/22* (2006.01)
(Continued)

(52) U.S. Cl.
CPC ........ *A61L 15/225* (2013.01); *A61F 13/00008* (2013.01); *A61F 13/00029* (2013.01); *A61F 13/00063* (2013.01); *A61L 15/44* (2013.01);
(Continued)

(58) Field of Classification Search
CPC ............... A61F 13/00029; A61F 2013/00604; A61F 13/000603; A61F 2013/0091
See application file for complete search history.

(56) References Cited

U.S. PATENT DOCUMENTS

| | | |
|---|---|---|
| 3,598,122 A | 8/1971 | Zaffaroni |
| 3,731,683 A | 5/1973 | Zaffaroni |
| 3,797,494 A | 3/1974 | Zaffaroni |

(Continued)

FOREIGN PATENT DOCUMENTS

| | | |
|---|---|---|
| CN | 1170564 A | 1/1998 |
| CN | 1545991 A | 11/2004 |

(Continued)

OTHER PUBLICATIONS

International Search Report corresponding to PCT Appl. No. PCT/US2014/012014 dated Mar. 14, 2014.

(Continued)

*Primary Examiner* — Susan Su

(57) ABSTRACT

A medical dressing containing an antimicrobial agent is disclosed. The medical dressing comprises a layered fabric comprising an inner layer of substantially hydrophilic material, an outer layer of substantially hydrophobic material on both sides of the inner layer; and an antimicrobial agent. The antimicrobial agent may be releasably impregnated into the fabric, coated on said fabric or a combination thereof. The antimicrobial agent may be a biguanide, such as polyhexamethylene biguanide (PHMB). The fabric inner layer material may be substantially a cellulose fiber, preferably substantially rayon, and the fabric outer layer material may be substantially polyester, e.g., a combination of textile matrix grade polyester fiber and amorphous binder grade polyester fiber. The fabric is preferably treated with an aqueous solution of surfactant and PHMB to have about 1500-3500 ppm of extractable PHMB.

10 Claims, 2 Drawing Sheets

(51) Int. Cl.
A61L 15/44 (2006.01)
A61L 15/46 (2006.01)

(52) U.S. Cl.
CPC ........ A61L 15/46 (2013.01); A61F 2013/0091 (2013.01); A61F 2013/00604 (2013.01)

(56) References Cited

U.S. PATENT DOCUMENTS

| | | |
|---|---|---|
| 3,978,855 A | 9/1976 | McRae et al. |
| 4,211,227 A | 7/1980 | Anderson et al. |
| 4,214,582 A | 7/1980 | Patel |
| 4,363,322 A | 12/1982 | Andersson |
| 4,541,426 A | 9/1985 | Webster |
| 4,643,180 A | 2/1987 | Feld et al. |
| 4,643,181 A | 2/1987 | Brown |
| 4,655,756 A | 4/1987 | Fawkes |
| 4,675,347 A | 6/1987 | Mochizuki et al. |
| 4,678,704 A | 7/1987 | Fellows |
| 4,681,577 A | 7/1987 | Stern et al. |
| 4,699,792 A | 10/1987 | Nick et al. |
| 4,769,013 A | 9/1988 | Lorenz et al. |
| 4,837,079 A | 6/1989 | Quantrille et al. |
| 4,984,570 A | 1/1991 | Langen et al. |
| 4,997,425 A | 3/1991 | Shioya et al. |
| 5,098,417 A | 3/1992 | Yamazaki et al. |
| 5,141,803 A | 8/1992 | Pregozen |
| 5,147,339 A | 9/1992 | Sundstrom |
| 5,151,314 A * | 9/1992 | Brown .................. A61B 19/088 128/849 |
| 5,156,843 A | 10/1992 | Leong et al. |
| 5,238,685 A | 8/1993 | Wren |
| 5,447,492 A | 9/1995 | Cartmell et al. |
| 5,465,735 A | 11/1995 | Patel |
| 5,466,231 A | 11/1995 | Cercone et al. |
| 5,498,416 A | 3/1996 | Carsenti-Etesse et al. |
| 5,633,007 A * | 5/1997 | Webb .................. A61F 13/023 424/443 |
| 5,686,096 A | 11/1997 | Khan et al. |
| 5,700,742 A | 12/1997 | Payne |
| 5,707,736 A | 1/1998 | Levy et al. |
| 5,759,570 A | 6/1998 | Arnold |
| 5,817,325 A | 10/1998 | Sawan et al. |
| 5,849,311 A | 12/1998 | Sawan et al. |
| 5,856,248 A | 1/1999 | Weinberg |
| 5,869,073 A | 2/1999 | Sawan et al. |
| 5,869,181 A | 2/1999 | Kent et al. |
| 5,886,048 A | 3/1999 | Kirschner et al. |
| 5,931,800 A | 8/1999 | Rasmussen et al. |
| 5,960,795 A | 10/1999 | Schultz |
| 5,985,931 A | 11/1999 | Modak et al. |
| 5,990,174 A | 11/1999 | Henry |
| 5,993,840 A | 11/1999 | Fawkes et al. |
| 6,017,561 A | 1/2000 | Zhou et al. |
| 6,025,287 A | 2/2000 | Hermann |
| 6,153,215 A | 11/2000 | Samuelsen et al. |
| 6,160,196 A | 12/2000 | Knieler et al. |
| 6,180,584 B1 | 1/2001 | Sawan et al. |
| 6,235,302 B1 | 5/2001 | Mans et al. |
| 6,333,093 B1 | 12/2001 | Burrell et al. |
| 6,369,289 B1 | 4/2002 | Orr, III |
| 6,503,524 B1 | 1/2003 | Tyrrell et al. |
| 6,599,525 B2 | 7/2003 | Scamilla Aledo et al. |
| 6,605,751 B1 | 8/2003 | Gibbins et al. |
| 6,689,931 B2 | 2/2004 | Etheredge, III |
| 6,700,032 B1 | 3/2004 | Gray |
| 6,762,213 B2 | 7/2004 | Lejeune et al. |
| 6,846,846 B2 | 1/2005 | Modak et al. |
| 6,869,537 B1 | 3/2005 | Nambu et al. |
| 6,949,595 B2 | 9/2005 | Morgan et al. |
| 6,991,848 B2 | 1/2006 | Thomson |
| 7,045,673 B1 | 5/2006 | Batich et al. |
| 7,417,000 B2 | 8/2008 | Barnabas et al. |
| 7,750,201 B2 | 7/2010 | Patel et al. |
| 7,799,965 B2 | 9/2010 | Patel et al. |
| 2002/0022660 A1 | 2/2002 | Jampani et al. |
| 2003/0014038 A1 | 1/2003 | Fine |
| 2003/0097103 A1 | 5/2003 | Horney et al. |
| 2003/0176827 A1 | 9/2003 | Chandra et al. |
| 2004/0015115 A1 | 1/2004 | Sinyagin |
| 2004/0028722 A1 | 2/2004 | Serafica et al. |
| 2004/0047763 A1 | 3/2004 | Kite et al. |
| 2004/0082925 A1 | 4/2004 | Patel |
| 2004/0110841 A1 | 6/2004 | Kite et al. |
| 2004/0142019 A1 | 7/2004 | Serafica et al. |
| 2004/0214495 A1 | 10/2004 | Foss et al. |
| 2004/0241216 A1 | 12/2004 | Klun et al. |
| 2005/0019380 A1 | 1/2005 | Hoon et al. |
| 2005/0048139 A1 | 3/2005 | Modak et al. |
| 2005/0058683 A1 | 3/2005 | Levy et al. |
| 2005/0106309 A1 | 5/2005 | Domazakis |
| 2005/0192547 A1 | 9/2005 | Modak et al. |
| 2005/0249791 A1 | 11/2005 | Hobbs et al. |
| 2005/0281762 A1 | 12/2005 | Modak et al. |
| 2006/0035039 A1 | 2/2006 | Ylitalo et al. |
| 2006/0129080 A1 | 6/2006 | Bjornberg et al. |
| 2007/0237812 A1 | 10/2007 | Patel et al. |
| 2010/0055437 A1* | 3/2010 | Fink .................. A61L 15/46 428/221 |
| 2012/0294920 A1 | 11/2012 | Gorka |
| 2012/0294927 A1 | 11/2012 | Gorka |
| 2013/0150765 A1 | 6/2013 | Moghe et al. |

FOREIGN PATENT DOCUMENTS

| | | |
|---|---|---|
| DE | 29723320 U1 | 8/1998 |
| EP | 0 136 900 A2 | 4/1985 |
| EP | 0531096 A2 | 3/1993 |
| GB | 899965 A | 6/1962 |
| GB | 2132939 A | 7/1984 |
| GB | 2194446 A | 3/1988 |
| GB | 2300200 A | 10/1996 |
| GB | 2321216 A | 7/1998 |
| JP | 08141010 | 6/1996 |
| JP | 2001-299807 A | 10/2001 |
| JP | 2001-340375 A | 12/2001 |
| JP | 04-317654 | 8/2009 |
| JP | 5-247814 B2 | 7/2013 |
| WO | 96/07783 A1 | 3/1996 |
| WO | 97/40717 A1 | 11/1997 |
| WO | 98/18330 A1 | 5/1998 |
| WO | 00/78883 A1 | 12/2000 |
| WO | 01/45615 A1 | 6/2001 |
| WO | 01/74300 A1 | 10/2001 |
| WO | 02/03899 A1 | 1/2002 |
| WO | 03/066001 A2 | 8/2003 |
| WO | 2004/037115 A2 | 5/2004 |
| WO | 2007120608 A2 | 10/2007 |
| WO | 2007120616 A2 | 10/2007 |
| WO | 2013/085640 A1 | 6/2013 |

OTHER PUBLICATIONS

International Search Report and Written Opinion for corresponding PCT application PCT/US07/08771, mailed Aug. 4, 2008.
First Office Action and English Translation issued in corresponding Chinese Application No. 200780013083.6 dated Jul. 6, 2010.
Third Office Action and English translation issued in corresponding Chinese Application No. 200780013083.6 dated Mar. 26, 2012.
Examiner's First Report issued in corresponding Australian Application No. 2007238827 dated Feb. 16, 2012.
EP Examination Report from Application No. 11 172 433.2 dated Dec. 9, 2013.
Patent Examination Report No. 1 from Australian Appl. No. 2009285774 dated Sep. 2, 2013.
Yani, et al., "Effects of ionic and surfactant agents on the antimicrobial activity of polyhexamethylene biguanide", Eye Contact Lens 37(2):85-89; Mar. 2011 (Abstract).
Chinese Office Action from Application No. CN200980139019.1 dated Feb. 26, 2014.

* cited by examiner

METHODS FOR PREPARATION OF MEDICAL DRESSING CONTAINING ANTIMICROBIAL AGENT

CROSS REFERENCE TO RELATED APPLICATIONS

This application is a continuation of and claims the benefit of priority under 35 U.S.C. §120 to U.S. patent application Ser. No. 13/330,092, filed Dec. 19, 2011, titled MEDICAL DRESSING CONTAINING ANTIMICROBIAL AGENT AND RELATED METHODS THEREFOR, which is a continuation of and claims the benefit of priority under 35 U.S.C. §120 to U.S. patent application Ser. No. 10/278,072, filed Oct. 23, 2002, titled MEDICAL DRESSING CONTAINING ANTIMICROBIAL AGENT, granted as U.S. Pat. No. 8,100,872 on Jan. 24, 2012, the entirety of each is hereby incorporated by reference for all purposes.

BACKGROUND OF THE INVENTION

1. Field of the Invention

The present invention relates to a medical dressing containing an antimicrobial agent, a sponge formed from such a dressing, and methods of fabricating such a medical dressing and sponge.

2. Brief Description of Art

Medical dressings have long been used to protect and aid in the healing of wounds. Various forms and constructions of such medical dressings are known in the art. For instance, U.S. Pat. No. 4,211,227, incorporated herein by reference, discloses a nonwoven surgical sponge material comprising a layered fabric having an inner core or a substantially hydrophilic material disposed adjacent at least one outer or surface layer, or between a pair of outer layers, of a substantially hydrophobic material. The sponge material is bonded by passing the material through rolls engraved in a pattern of lands and grooves such that a repeating pattern of three degrees of compression are imposed on the material.

U.S. Pat. No. 6,369,289, incorporated herein by reference, further discloses the use of a cellulosic bandage in a method for covering an open wound by contacting the wound with the bandage having a calculated amount of antimicrobial agent. The cellulosic bandage may be prepared by providing at least one rolled beam of cellulosic material onto a perforated drum, inserting the beam of material into an enclosed vessel, adding antimicrobial agent into the vessel, and circulating the antimicrobial agent for a predetermined period of time.

The use of certain kinds of antimicrobial agents is also known in the art. U.S. Pat. No. 4,655,756, for example, relates to a non-woven material treated with a linear polymeric biguanide having a defined formula, or a mixture of, e.g., polyhexamethylene biguanide (hereafter "PHMB") dihydrochlorides with defined number average molecular weights. The polymeric biguanide may be present at a concentration of from 500 to 5000 ppm and the non-woven material may be in the form of an article for the collection of human body emissions.

Other types of antimicrobial agents are also known. For example, U.S. Pat. No. 5,707,736 discloses a dry, disposable, polymeric product having sustained-release antimicrobial activity formed from a polymeric material having an amine salt antimicrobial agent incorporated therein. The polymeric material may be in the form of fibers, sheets, films, and other stable woven, nonwoven and knitted materials. The antimicrobial agents include, e.g., chlorhexidine gluconate and chlorhexidine hydrochloride.

Additional components, such as adhesives, are also known as components of medical dressings. One such surgical dressing is described in U.S. Pat. No. 4,643,180, wherein the dressing comprises a sheet of polymeric film coated on one side with a water based adhesive of defined thickness which includes an antimicrobial agent deposited on the body facing surface of the adhesive.

U.S. Pat. No. 4,643,181 also describes a surgical dressing and a process for making a surgical dressing. The dressing comprises a substrate coated on one surface with a solvent-based skin contact adhesive of defined thickness, the adhesive having distributed therein particles of PHMB. The process involves mixing a defined aqueous solution of PHMB hydrochloride with a solvent which is compatible with the adhesive at a mixing speed of no more than 300 rpm, adding the mixture to an adhesive, applying the adhesive to a release surface in an amount of from 40 to 55 grams per square meter, drying the adhesive, and applying a substrate for the dressing to the adhesive.

U.S. Pat. No. 4,675,347 relates to an antimicrobial latex composition and a method of manufacturing a shaped article by repeatedly dipping an article into the composition and drying. The composition comprises, e.g., (1) at least one cationic latex component selected from a cationic natural rubber latex and a cationic synthetic polymer latex and (2) a cationic antimicrobial agent incorporated in the cationic latex (1).

U.S. Pat. No. 4,678,704 describes an impregnated fabric material comprising a fabric substrate to which has been bonded an active cationic impregnant along with an anionic indicator dye in combination with a further cationic component, wherein the dye bonds to the further cationic component more readily than to the substrate and the further cationic component competes with the impregnant for bonding to the dye. The cationic impregnant may be a polymeric biguanide, e.g., PHMB.

U.S. Pat. No. 4,837,079 relates to a method for making an antimicrobially active, non-woven web comprising the steps of fainting an unbounded fibrous web, applying throughout the unbonded fibrous web an uncured binder and PHMB hydrochloride as an antimicrobial agent, the PHMB hydrochloride being substantive to the fibers of the web and to the binder when the web is either wet or dry to prevent the antimicrobial agent from substantially diffusing from the fibers or binder and being present in an amount effective to act as antimicrobial agent, and curing the binder to bind the fibers together to form an antimicrobially active, non-woven web. An antimicrobially active, non-woven web comprising bonded fibers, a binder distributed throughout the fibers in an amount effective to bind the fibers and PHMB hydrochloride which is substantially prevented from diffusing from the fibers or the binder is also disclosed. Further disclosed is a wet wiper that is substantially identical to the claimed web, but which additionally contains a substantially preservative free liquid.

U.S. Pat. No. 5,098,417 relates to a wound dressing for systemic administration of a physiologically- or biologically-active agent by controlled release of the agent into such wound. The wound dressing comprises a substrate in the form of a fabric or cloth, at least a portion of which is cellulosic, which has been chemically modified to convert hydroxyl groups in the cellulosic portion to ionic-adsorbing sites, an ionic form of a physiologically- or biologically-active agent (which includes antibacterial agents) adsorbed in the substrate. The ionic bonds hold the agent temporarily to the substrate for controlled release therefrom in proportion to the amount of exudate in contact with the substrate and are formed by adsorbing the agent on the substrate at room temperature. The ionic bonds are disassociated upon contact with body exudate from wounds thereby to release the physiologically- or biologically-active agent in an amount in proportion to the amount of exudate in contact with the substrate. Chlorhexidine is mentioned as one of the possible agents.

U.S. Pat. No. 5,141,803 relates to a moistened wipe for cleaning and delivering a cationic biocide comprising a flexible absorbent nonwoven substrate impregnated with an aqueous composition comprising defined amounts of potassium sorbate, citric acid, disodium ethylenediaminetetraacetate, a cationic biocide selected from a defined group which includes PHMB hydrochloride and the remainder water. The pH of the composition is from about 3.5 to about 4.5.

U.S. Pat. No. 5,156,843 relates to a composition of matter comprising a material provided with interstices having solid particles residing therein. The material is a member selected from the group consisting of joined fibers, woven fabric, non-woven fabric, paper, woven cloth, non-woven cloth, foamed plastic and sponge. The solid particles are from about one to about 100 microns in diameter and contain a substantially continuous network of pores open to the exterior of the particles, with a functional substance retained in the pores. The functional substance may be a biocidal substance that can prevent or retard bacterial, microbial, germ or fungal growth.

U.S. Pat. No. 5,498,416 relates to a process for protection of prostheses, implants and/or catheters, of temporary or permanent implantable materials against bacterial colonization and infection. An infection-resistant device capable of progressively releasing in aqueous medium an amount of an antibacterial substance fixed to the device, the amount being effective to prevent bacterial contamination of the device is disclosed. The device comprises a first coating from a solution in aqueous or organic solvent of a biguanide of a defined general formula (which defines monomeric compounds) and a second coating from a solution of the antibacterial substance, the second coating overlying the first coating, and the first coating ensuring adhesion of the antibacterial substance to the device. Illustrative devices are described in the paragraph beginning at column 2, line 60 and include urinary catheters, probes, vascular and intraarterial catheters, cardiacal valvular prostheses, arterial prostheses, cardiac simulators, orthopedic prostheses, ocular or dental implants, shunts that are connecting two segments of the circulatory system, and suture thread.

U.S. Pat. No. 5,700,742 relates to a method of treating a textile material to inhibit microbial growth which comprises applying to the textile material an oligo- or polymeric biguanide or salt thereof with an inorganic acid or an organic acid having a pK value above 4.5 followed by a strong organic acid having a pK value below 4.5 and free from any aliphatic or oxyalkylene chain containing 12 or more carbon atoms. A textile material treated in accordance with the claimed method is also disclosed.

U.S. Pat. No. 5,856,248 relates to cellulose fibers and products comprising cellulose fibers treated to absorb body secretions while substantially decreasing microbial growth, the fibers being chemically modified in a two-stage process comprising a first stage treatment with a water soluble salt of a transition metal and an alkali and a second stage treatment with a solution of a bisbiguanide compound, thereby forming a bond between the cellulose fibers, the transition metal and the bisbiguanide compound. The process may utilize a rinsing step to neutral pH between the two aforementioned stages.

U.S. Pat. No. 5,869,073 relates to a liquid composition for applying a non-leachable antimicrobial layer or coating on a surface, comprising a solution, dispersion or suspension of a biguanide polymer, a cross-linker reacted with the biguanide polymer to form an adduct, and an antimicrobial metal, metal salt (e.g. a silver salt) or metal complex, wherein the metal, metal salt or metal complex forms a complex with the adduct, and wherein the antimicrobial layer or coating does not release biocidal levels of leachables into a contacting solution.

U.S. Pat. No. 5,817,325 relates to an article of manufacture having disposed on a surface thereof a contact-killing, non-leaching antimicrobial coating which kills microorganisms upon contact. The coating comprises an organic polycationic polymer matrix immobilized on the surface having bound or complexed thereto a surface-accessible antimicrobial metallic material such that the antimicrobial material does not release biocidal amounts of elutables into the surrounding environment. The organic matrix may comprise a biguanide polymer, such as PHMB or a polymer containing a biguanide moiety.

U.S. Pat. No. 5,849,311 further relates to a contact-killing, non-leaching antimicrobial material, capable of killing microorganisms which come into contact with the material. The material comprises an organic polycationic polymer matrix having non-leachably bound or complexed thereto an antimicrobial metallic material, such that the antimicrobial material does not release biocidal amounts of elutables into the surrounding environment. The polycationic material may be PHMB or a polymer containing a biguanide moiety.

U.S. Pat. No. 5,886,048 relates to a method of treating tumor disease in a human or animal with a therapeutically effective amount of PHMB or salt thereof.

U.S. Pat. No. 5,985,931 relates to an antimicrobial composition comprising defined amounts of PHMB, a quaternary ammonium compound; and parachlorometaxylenol wherein the combination of the three components is said to exhibit effective antimicrobial activity.

U.S. Pat. No. 5,990,174 relates to a method for improving haze formation and storage stability of an antimicrobial composition consisting of water and from 5 to 25% by weight of defined linear polymeric biguanide oligomers. The method comprises adjusting the pH of the aqueous antimicrobial composition to at least 0.1 and less than 5 as determined using an indicator thereby improving the resistance to haze formation and storage stability of the aqueous antimicrobial composition when compared with a corresponding composition at higher pH. Particular concentration and pH limitations are also disclosed.

U.S. Pat. No. 5,993,840 relates to a composition comprising a non-woven material containing a mixture of polymeric biguanides subject to desorbtion when the non-woven material is wetted by urine; and an anionic polymer which is substantially insoluble in urine. The anionic polymer functions to retain the biguanides on the material when contacted by urine. A process for forming an absorbent layer and a method of reducing the loss of antimicrobial biguanide, wherein both include the anionic polymer, are disclosed.

European Patent Application No. 136900 discloses the application of PHMB to a surgical drape comprising a non-woven fabric and mentions on page 7 that a non-ionic wetting agent in the application formulation is desirable to provide absorbent characteristics to the fabric.

U.S. Pat. No. 6,017,561 relates to an antibacterial cleaning composition comprising a quaternary ammonium compound, an anionic polymer having an acid number greater than 10 wherein the anionic polymer is partially or completely neutralized by quaternary ammonium compound to form a polymer complex and wherein the polymer complex is greater than about 15% by weight of the solids in the composition, a dispersing agent, which comprises a surfactant that is selected from the group consisting of nonionic surfactant, amphoteric surfactant, and mixtures thereof, and optionally, a solvent. Also disclosed is a sponge device having antibacterial activity that comprises a sponge; and a polymer complex comprising a quaternary ammonium compound and an anionic polymer having an acid number of greater than 10 wherein the anionic polymer is partially or completely neutralized by the quaternary ammonium compound to form the polymer complex which is attached to a surface of the sponge. An adsorbent or absorbent matrix which includes the polymer complex and a method of fabricating an absorbent or adsorbent material which uses at least a quaternary ammonium compound and an anionic polymer are also disclosed. The ammonium compound may be PHMB hydrochloride. Articles such as sponges are also described.

U.S. Pat. No. 6,160,196 relates to a wound covering comprising a hydrophobic, bacteria-absorbing synthetic or naturally-occurring polymer fiber material, having adhered thereto an antimicrobial active compound which is adapted to not be released into the wound. As described in the specification and included in certain dependent claims, the material can be nonwoven and dependent claim 10 recites that the polymer fiber material can be selected from a group which includes polyester. The antimicrobial active compounds are described in the passage that begins at column 2, line 29 and include chlorhexidine. In this passage, it is stated the compounds " . . . are distinguished by the fact that they adhere firmly to the wound covering and are not released, or at least are not released noticeably, into the wound."

U.S. Pat. No. 6,180,584 relates to a disinfectant composition comprising a film-forming antimicrobial material (which may be a polymeric biguanide material), an antimicrobial metallic material, and a carrier. The composition, when applied to a surface, forms a non-permanent, adherent, water-insoluble film, wherein the metallic material is non-leachably bound to or associated with the film. The film does not elute antimicrobial materials into contacting water at levels capable of imparting disinfecting action to said water, and is removable by treatment with an alcohol solution. The composition can further include a surfactant.

U.S. Pat. No. 6,235,302 relates to a sponge cloth which is based on regenerated cellulose and has been provided with an internal reinforcement consisting of, e.g., viscose fibers or cotton fibers having a staple fiber length of 5 to 50 mm. The sponge cloth is obtained by a process comprising the steps of coagulating and regenerating the cellulose in a bath which has a pH of 13 or higher and which comprises Glauber's salt, NaOH and water, and impregnating the sponge cloth with a biocidally active agent. Representative agents are described and include isothiazolone, benzoisothiazolone and benzimidazole derivatives with biguanides.

OBJECTS AND SUMMARY OF THE INVENTION

It is an object of the present invention to provide a medical dressing comprising an antimicrobial agent as well as a process of making such a medical dressing. It is a further object to provide a sponge formed from the medical dressing as well as a process of making such a sponge.

The medical dressing and sponge formed therefrom are preferably characterized by improved antimicrobial behavior. More particularly, in a preferred embodiment, the medical dressing and sponge formed therefrom provide an effective antimicrobial barrier for a wound while also controlling the release of antimicrobial agent contained within an inner portion of the dressing. The antimicrobial agent is preferably concentrated within an inner portion absorbent core of the dressing while an outer barrier layer portion reduces the release of the antimicrobial agent from the dressing.

It is a further object of the invention to provide a medical dressing and a sponge formed therefrom wherein the outer hydrophobic layer(s) provide(s) non-adherent surfaces to aid in the healing of wounds and which reduces or eliminates pain experienced by a patient during changes in the dressing or sponge.

In accordance with one aspect of the present invention, a medical dressing is provided, comprising:
    layered fabric comprising:
    an inner layer of substantially hydrophilic material;
    an outer layer of substantially hydrophobic material on both sides of the inner layer; and
    an antimicrobial agent, wherein the antimicrobial agent is contained in the inner layer.

In accordance with another aspect of the invention, the medical dressing of the invention may be in the form of a sponge comprising plies of the medical dressing material.

DETAILED DESCRIPTION OF THE PREFERRED EMBODIMENTS OF THE INVENTION

In one embodiment, the inventive medical dressing is based in part upon the dressing disclosed in U.S. Pat. No. 4,211,227, the disclosure of which is incorporated herein by reference in its entirety.

Figure 1:
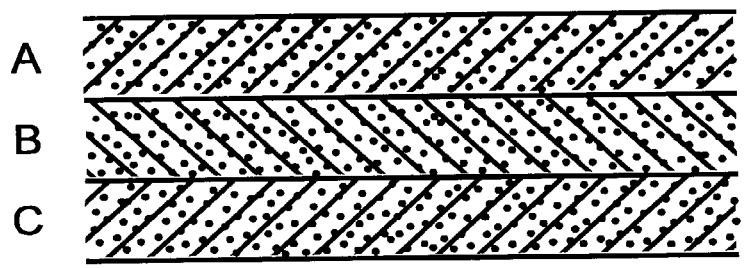
FIG. 1 illustrates a cross-sectional view of one form of the medical dressing containing two outer layers and an inner layer.

In a preferred embodiment, the inventive medical dressing is an antimicrobial drain sponge which is a thermally bonded nonwoven absorbent material, typically in the form of a square that is 2"×2" or 4"×4" and having a 6 ply thickness. The material is preferably about 50% polyester and about 50% rayon with each ply formed as a sandwich of a layer of rayon between two layers of polyester. In one embodiment of the invention, as illustrated in FIG. 1, the outer layers (A and C) may be formed from a hydrophobic material, preferably hydrophobic fibers, such as polyester fibers. The inner layer (shown as layer B in FIG. 1) comprises a hydrophilic material, preferably hydrophilic fibers, such as cellulosic fibers. More preferably, the cellulosic fibers are rayon.

In order to impart antimicrobial properties, the material that is to be cut into the individual sponges is impregnated with an aqueous solution of an antimicrobial agent, such as polyhexamethylene biguanide (PHMB). An antimicrobial agent such as PHMB is suitably present in a concentration of about 0.1 to 0.5% by weight, preferably about 0.15 to 0.35% by weight, and most preferably about 0.2 to 0.3% by weight. A surfactant may also be present in the aqueous solution. For example, commercially available non-ionic surfactants, such as TWEEN® 20, which is polyoxyethylene (20) sorbitan monolaurate, may be utilized. PHMB used to prepare the drain sponge may be provided by, e.g., Avecia Inc. under the designation COSMOCIL® CQ (an aqueous solution of PHMB containing 19-21% w/w active ingredient and a pH of 5.0-5.5). The material may be impregnated with the antimicrobial agent according to any suitable technique, such as, e.g., by dip coating the material in a solution comprising the antimicrobial agent.

Figure 2:
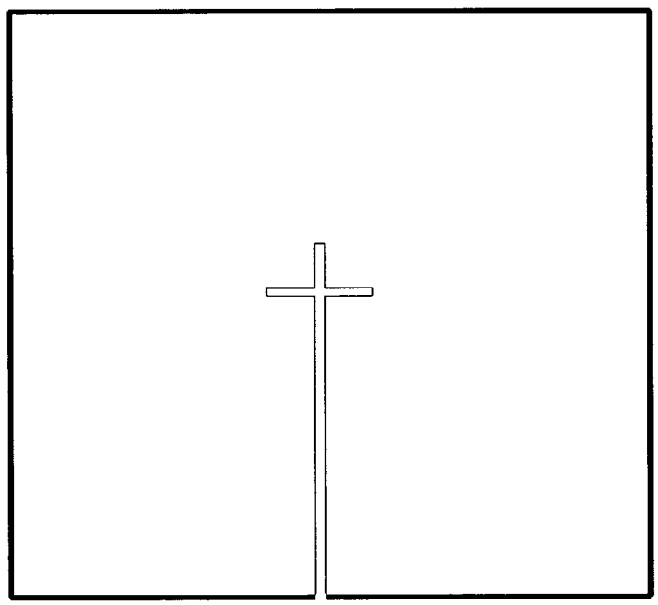
FIG. 2 illustrates a surface view of one form of the medical dressing containing a cross-shaped incision passing through all plies of the dressing.

The impregnated material may then be pressed at a pressure designed so that the appropriate level of antimicrobial agent, preferably PHMB, remains in the material. After drying by passing between heated rollers, the material has a residual antimicrobial agent (e.g. PHMB) content of from 1500 to 3500 ppm. The material is subsequently converted into 4"×4" and 2"×2", 6 ply drain sponges. The sponges do not include an adhesive, but have a cross-shaped incision in the center (as illustrated in FIG. 2) that penetrates all 6 plies so that a drain tube can be passed therethrough. The antimicrobial agent (e.g. PHMB) can preferably be released from the medical dressing or sponge in a moist environment to provide antimicrobial activity beyond the edges of the sponge for a limited time. In general, the fabric is treated to have about 1500-3500 ppm of extractable antimicrobial agent, preferably polyhexamethylene biguanide.

The antimicrobial agent is preferably releasably impregnated into the inner layer substantially hydrophilic material of the fabric, coated on said inner layer or a combination thereof. The antimicrobial agent is also preferably controllably releaseable from the fabric in an amount effective as an antimicrobial, more preferably in amount effective as an antimicrobial for a period of up to about 2 days, most preferably up to about 1 day. The antimicrobial amount is defined as the amount of antimicrobial agent applied to the dressing that is needed for providing sufficient antimicrobial characteristics, yet without causing irritation of the skin or open wound.

Although the antimicrobial agent may be released from the inner layer material of the fabric, the antimicrobial treatment of the fabric principally allows the dressing to function as a barrier to contamination of the wound from sources outside the wound. In addition, due to the absorbent characteristics of the dressing, microbes absorbed within the inner layer are prevented from escaping through the dressing.

In general, the antimicrobial agent may be any such agent which suitably functions to provide an antimicrobial property to the inventive medical dressing. Such antimicrobial agents are described in some of the above-identified patents, which are herein incorporated by reference for such information. Preferred antimicrobial agents include biguanides, especially polyhexamethylene biguanide ("PHMB").

The fabric inner layer material is substantially hydrophilic, and is preferably substantially a cellulose fiber, and, more preferably, is substantially rayon. Other inner layer materials may also be utilized, including polysaccharides, alginates, cotton or carboxy methyl cellulose fiber materials. In general, the inner layer material is "substantially hydrophilic" such that wound exudate may be absorbed by the inner layer absorbent core and that the antimicrobial agent may be contained mostly within the absorbent core. In this way, the term "substantially hydrophilic" describes the function of the inner layer material. It also distinguishes the inner layer material over the function of the "substantially hydrophobic" outer layer material, which provides an antimicrobial barrier property and attenuates or reduces the release of antimicrobial agent away from the dressing. The improved retention of antimicrobial agent within the inner layer also lowers the bioburden, i.e., the growth and number of cells, within the dressing during use.

Hydrophobicity and hydrophilicity are commonly reported as the percentage moisture regain for fibers of the material. For the purposes of the present invention, the terms "substantially hydrophilic" and "substantially hydrophobic", as they apply to the inner and outer layers respectively, may be related to the percentage moisture regain for fibers of the respective materials, typically at 70° F. and 65% relative humidity. The fibers used in the substantially hydrophobic outer layer should have a moisture regain of less than about 10%, preferably less than about 5%, and most preferably less than about 2% based on the weight of the dry fiber. The fibers used in the substantially hydrophillic inner layer should have a moisture regain of about 5-25, preferably about 10-20, and most preferably about 15-20 times the weight of the dry fiber.

The fabric outer layer material is preferably substantially polyester, and, more preferably, is a combination of textile matrix grade polyester fiber and amorphous binder grade polyester fiber. The binder fibers function to bind, e.g., rayon and textile grade polyester fibers together. Suitable inner layer materials include, e.g., Lenzing 8191 rayon. Suitable outer layer materials include, e.g. Wellman Polyester T-203 textile grade polyester and Kosa Polyester 259 amorphous binder grade polyester. The textile to binder fiber weight ratio is preferably about 2:1. Other materials may also be utilized for the outer layer, including, e.g., polyolefins such as polyethylene or polypropylene, nylons, or other thermoplastic fibers.

The hydrophobic layers of the fabric forming the medical dressing may also be imparted with a hydrophilic finish. Such a finish may be applied as a coating of a hydrophilic finishing agent on the outer layers. It may also be applied during the impregnation of the inner layer with the antimicrobial agent by including the hydrophilic finishing agent in the same solution of antimicrobial agent. By contacting the dressing material with the antimicrobial solution containing a hydrophilic finishing agent, the inner layer is impregnated with the antimicrobial solution while the outer layers are imparted with a hydrophilic finish. As used herein, the term "hydrophilic finish" is intended to mean that the hydrophilic characteristics of the outer layer are increased at least to some degree by the use of a hydrophilic finishing agent. In a preferred embodiment, the hydrophilic finish helps to improve the function of the dressing material or sponge by allowing wound exudate to be more easily absorbed by the inner layer absorbent core material. Suitable hydrophilic finishing agents include, e.g., surfactants, such as non-ionic surfactants, which may be typically applied in concentrations of about 0.1% by weight. As noted above, one such non-ionic surfactant is TWEEN® 20, which is polyoxyethylene (20) sorbitan monolaurate, although other such surfactants may also be utilized.

A medical sponge formed from plies of the medical dressing material may contain several plies of the dressing material, preferably 2-10 plies, more preferably 4-8 plies, and most preferably 6 plies. A cross-shaped incision may be preferably formed in the center of the sponge that penetrates all plies, thereby allowing an object to pass through the sponge.

In a preferred aspect, the fabric comprises about 50% by weight rayon, about 33% by weight textile matrix grade polyester, and about 17% by weight binder grade polyester, based on the weight of the fabric.

The fabric of the medical dressing and sponge of the invention may be processed to impart softness and improved absorbency, according to techniques known in the art, followed by further processing to form the inventive medical dressing and sponge. Suitable techniques include the use of microcreping devices such as are commercially available from Micrex, Corp. for the treatment of nonwoven and other materials. It is preferred that such treatments provide an absorbency of from about 6-15, preferably 10-15, times the dry weight of the fabric. As used in the context of the invention, the term "absorbency" refers to the amount of liquid material, such as water or wound exudate, that may be absorbed by the fabric of the medical dressing or sponge.

As compared with other commercial medical dressings and sponges, the present invention provides several advantages and benefits. For example, by containing the antimicrobial agent within the inner layer of the medical dressing and the sponge formed therefrom, the release of the antimicrobial agent is controlled such that sensitive wound or skin areas are not adversely irritated. The presence of the antimicrobial agent within the inner layer also allows for the dressing and sponge to function effectively as a barrier against contamination of the wound. Contamination of areas outside the wound and dressing or sponge due to the retention of the wound exudate within the dressing or sponge is also reduced or prevented. In addition, the use of the outer hydrophobic (nonwoven) layers provides the dressing and sponge with the characteristic of non-adherency to wounds. Further, due in part to the presence of the outer hydrophobic layer(s), the amount of antimicrobial agent within the inner layer necessary to maintain the antimicrobial effectiveness of the dressing or sponge is also reduced compared with other commercial products. As such, the present invention provides a benefit of reduced cost associated with the use of lesser amounts of antimicrobial agent.

The medical dressing of the present invention may also comprise layered fabric consisting essentially of an inner layer of substantially hydrophilic material; an outer layer of substantially hydrophobic material on both sides of the inner layer; and an antimicrobial agent, wherein the antimicrobial agent is contained in the inner layer. As used in the context of the invention, the phrase "consisting essentially of" is intended to mean that the certain additional components which would materially affect the basic and novel characteristics of the inventive medical dressing are not included in the layered fabric. As concerns the medical dressing and sponge of the invention, "consisting essentially of" is intended to mean, e.g., that adhesives are not utilized to prepare the layered fabric or that additional agents are not utilized to bind the antimicrobial agent within the inner layer material of the medical dressing.

EXAMPLES

The antimicrobial efficacy of the medical dressing and sponge according to the invention has been investigated. Such tests simulate the use of the dressing or sponge in practice and are based upon the visual observation of microbial activity on growth media placed in contact with the inventive medical dressing or sponge containing a determined amount of microbes. The tests are generally conducted by placing a sample of the antimicrobial agent containing dressing or sponge in contact with growth medium, adding a small volume of microbe containing aqueous solution to the medical dressing or sponge, and incubating the test samples for definite time periods and under controlled temperature and environmental conditions. Following the end of the pre-determined time period, the growth medium is visually observed to determine the extent, if any, of microbial activity or growth on the medium. For the purposes of the present invention, an assessment of the antimicrobial effectiveness of the inventive dressing and sponge against various microbes, including *S. aureus, S. epidermidis, E. coli*, and *P. aeruginosa*, has been conducted according to this procedure. In all such tests, the medical dressing and sponge according to the invention has been determined to be effective to prevent microbial activity on such growth medium. By comparison, control samples not containing an antimicrobial agent, such as PHMB, were determined using the same procedures and conditions to not prevent microbial activity on such growth medium.

While the invention has been described in detail by reference to specific embodiments, the skilled artisan will appreciate that various modifications, substitutions, omissions and changes may be made, and equivalents employed, without departing from the spirit of the invention or the scope of the appended claims.

What is claimed is:

1. A method of preparing a medical dressing comprising:
   forming a layered fabric consisting essentially of
      an inner layer of hydrophilic material, and
      outer layers of hydrophobic material on both sides of the inner layer; and
   impregnating a biguanide antimicrobial agent into the inner layer.

2. The method according to claim 1 wherein the inner layer of hydrophilic material is rayon, and the outer layers of hydrophobic material are a combination of textile matrix grade polyester fiber and amorphous binder grade polyester fiber.

3. The method according to claim 2, wherein impregnating the biguanide antimicrobial agent comprises contacting the layered fabric with a solution having a surfactant and polyhexamethylene biguanide.

4. A method comprising forming a dressing consisting essentially of an inner layer of hydrophilic material, outer layers of hydrophobic material on both sides of the inner layer, and a biguanide antimicrobial agent, wherein the biguanide antimicrobial agent is releasably contained in the inner layer.

5. The method of claim 4, wherein the biguanide antimicrobial agent is polyhexamethylene biguanide.

6. The method of claim 5, wherein at least one outer layer is a combination of textile matrix grade polyester fiber and amorphous binder grade polyester fiber.

7. The method of claim 4, wherein the hydrophilic material is rayon, and the hydrophobic material is a combination of textile matrix grade polyester fiber and amorphous binder grade polyester fiber.

8. A method of preparing a sponge comprising forming layered plies of a substrate consisting essentially of at least one inner layer of hydrophilic material, outer layers of hydrophobic material on both sides of the at least one inner layer, and a biguanide antimicrobial agent releasably contained in the inner layer.

9. The method of claim 8, wherein the biguanide antimicrobial agent is polyhexamethylene biguanide.

10. The method of claim 8, further comprising creating a cross-shaped incision at the center of the layered plies.

* * * * *